United States Patent [19]

Edenbaum et al.

[11] Patent Number: 5,171,208
[45] Date of Patent: Dec. 15, 1992

[54] CASTING OR SPLINTING DEVICE AND METHOD OF MAKING SAME

[75] Inventors: Martin Edenbaum, Princeton Junction, N.J.; James L. Clark, West Chester, Pa.

[73] Assignee: Carapace, Inc., Tulsa, Okla.

[21] Appl. No.: 700,555

[22] Filed: May 15, 1991

[51] Int. Cl.⁵ ............................................... A61F 5/04
[52] U.S. Cl. ............................................ 602/6; 602/58
[58] Field of Search ................. 128/877, 878, 83, 77, 128/85, 87 R, 89 R-91 R, 156; 604/368, 369, 378; 602/6, 7, 8, 900, 58, 20-27

[56] References Cited

U.S. PATENT DOCUMENTS

| | | | |
|---|---|---|---|
| 4,235,228 | 11/1980 | Gaylord | 128/91 R |
| 4,306,549 | 12/1981 | Canie | 128/90 |
| 4,989,593 | 2/1991 | Campagna | 128/89 R |
| 5,016,622 | 5/1991 | Norvell | 128/91 R |
| 5,027,803 | 7/1991 | Scholz | 128/89 R |

Primary Examiner—Robert A. Hafer
Assistant Examiner—David J. Kenealy
Attorney, Agent, or Firm—Head & Johnson

[57] ABSTRACT

A unitary splinting and casting device pre-formed in layers with a patient contact layer, padding layer, cast layer and fabric layers and a method of making the device. The device is unitary, in the sense that it is pre-formed and packaged so that no additional materials or components are needed to use it.

29 Claims, 1 Drawing Sheet

U.S. Patent            Dec. 15, 1992            5,171,208
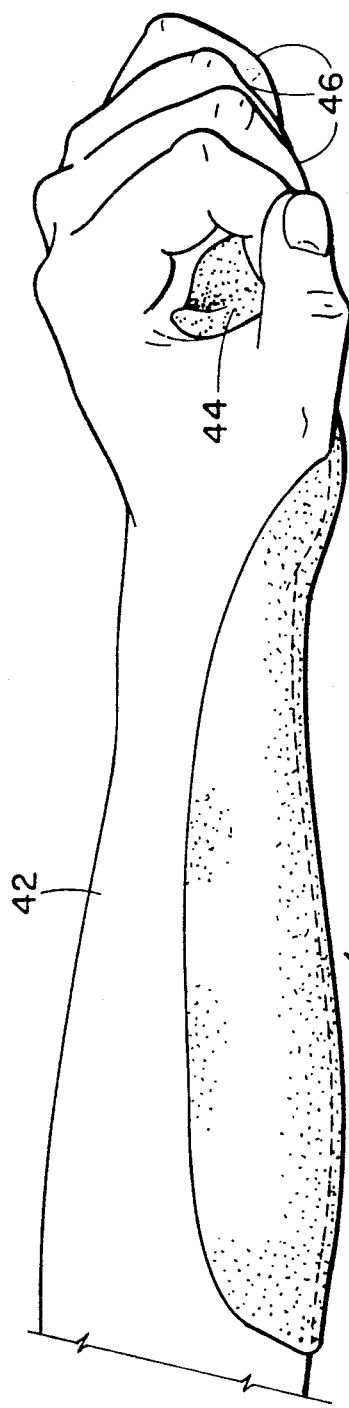
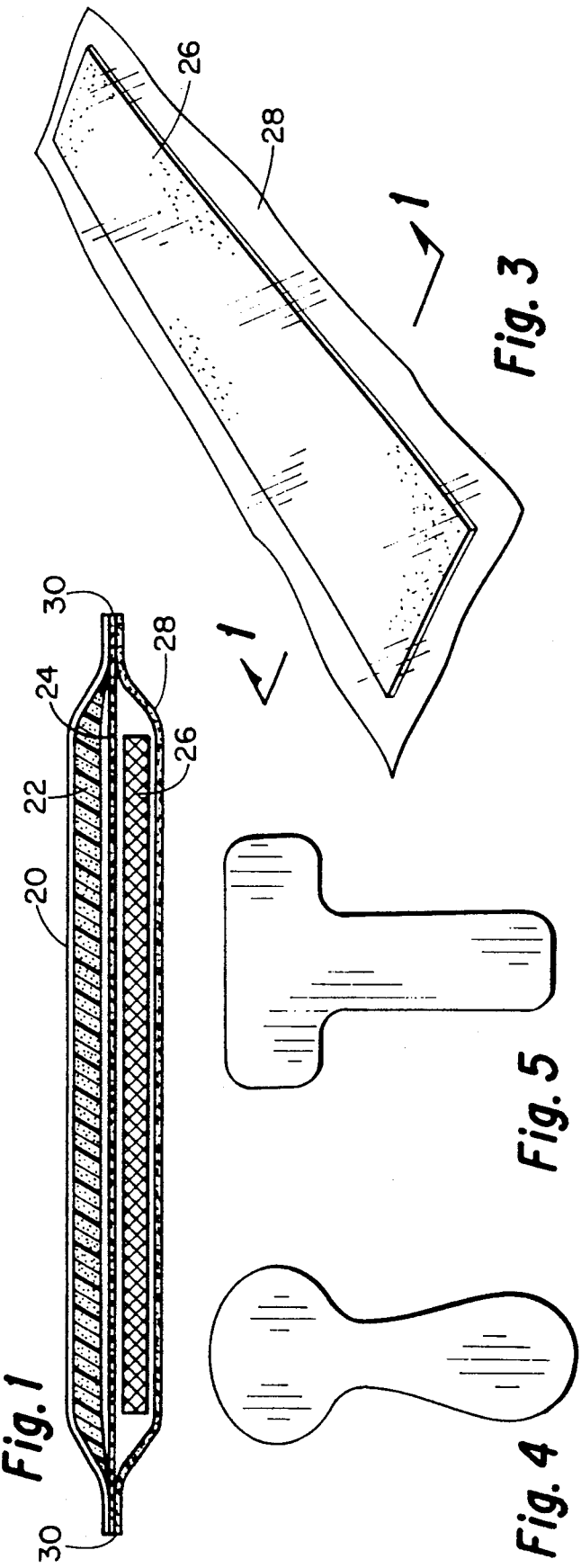

CASTING OR SPLINTING DEVICE AND METHOD OF MAKING SAME

The following materials are disclosed pursuant to 37 CFR 1.97–1.99:

| U.S. Pat. Nos.: | | |
| --- | --- | --- |
| 4,193,395 | Gruber | 03/18/80 |
| 4,235,228 | Gaylord et al. | 11/25/80 |
| 4,442,833 | Dahlen et al. | 04/17/84 |
| 4,454,874 | Monnier | 06/19/84 |
| 4,628,917 | Campagna, Jr. et al. | 12/16/86 |
| 4,770,299 | Parker | 09/13/88 |
| 4,869,046 | Parker | 09/26/89 |
| 4,899,738 | Parker | 02/13/90 |

Gruber requires covering the area to be cast with stockinette, wrapping the area with casting material, then cutting or splitting the cast to form a splint. The casting material used is epsilon polycapriolactone and the padding material used is elastic foam.

Gaylord uses plaster casting material, encloses the casting material in a tubular stockinet [sic] and fastens the materials together with a line of stitching.

Dahlen uses a porous, water-permeable envelope (such as stockinette) to surround his casting material; this layer contacts the skin of the patient.

Monnier uses plaster casting material, a water impermeable sheath completely surrounding the casting material—with holes in the side away from the patient, "bubbles" or cushioning material external to this on the patient side, and a heat shield.

Campagna uses a two part device with the first part being mesh and resin enclosed in fabric, and the second part a foam padding with adhesive surface which is applied after the first part is wet and ready to use.

Parker ('299) uses a tubular moisture impervious wrapping or sleeve around a settable core which is the same on both the patient and non-patient side, is in a roll, and sealed in foil.

Parker ('046) uses a tubular wrapping around the layer of casting material, which is also the patient contact layer and the external non-patient contact layer when applied. A foam or padded layer is not used.

Parker ('738) is similar to the above Parker ('299) patent, but also claims flexible padding on both sides of the device.

BACKGROUND OF THE INVENTION

1. Field of the Invention

The present invention relates generally to the field of orthopedic casts and splints used to immobilize a body part, and more particularly to a unitary preformed multilayer casting or splinting device and method of forming such.

2. Description of the Related Art

In the older art, casting typically required multiple steps: covering that part of the body to be immobilized with padding and a waterproof layer, soaking strips of casting material and applying them to the body over the above layers, smoothing the surfaces, and allowing it to dry and cure. The same process was used for splints, but part of the finished cast was cut away after forming to make the splint (as described in Gruber). This process required stocking padding, waterproofing, casting resin or plaster of paris, etc., and was time consuming, messy and required some skill and training.

To overcome these problems, various unitary products have been devised, as illustrated in the above listed patents. Several of these (Gaylord, Parker '299 and Parker '738) use stockinette or tubular material to enclose the casting material. The problem with a tubular sheath, is that it restricts the width of the device to that of the sheath. Inserting the inner layer(s) into a sheath can be difficult, and if various widths are to be used, one must obtain and keep an inventory of various sizes of sheathing material. Further, such tubular sheathing presents the same material on all sides of the device, so that the patient side and the non-patient side are covered with the same material. Finally, the use of tubular sheathing precludes the formation of a variable outline of the device, i.e., wedge-shape, curved sides, serpiginous shapes, "T" shapes, "V" shapes, "H" shapes, and the like. A further disadvantage of using the same material, either as a sheath or internally, on both sides of the device, is that if the material is padding (as in Parker '299), it unnecessarily increases the thickness, bulk and cost of the device, since padding is only needed on the patient side of the device.

Further problems with some unitary casting devices is that the patient contact surface is waterproof. This allows moisture to build up under the cast or splint and can cause skin damage or infection. Other devices have attempted to solve this problem by making the patient contact surface out of fabric that absorbs moisture or is hydrophilic. This can cause excess moisture to be absorbed and held against the patient's skin.

Yet another disadvantage of some devices, is that the various layers of the device are made of material that not only allows water to pass freely through the layer(s), but are also hydrophilic (such as fabric stockinette, and the like); this causes retention of excess moisture when the device is wetted prior to use, such that the device must be wrung out, and results in prolonged drying times.

Once the unitary product is made, it is usually sealed in a waterproof container, such as foil or plastic, to keep the resin or casting material from getting moist and setting prematurely. If the casting material used is plaster of paris, sealing is less important than with synthetic resin casting material.

SUMMARY OF THE INVENTION

It is an object of this invention to provide a unitary casting or splinting device that has a water impervious, but vapor penetrable, non-hydrophilic or substantially hydrophobic layer on the patient contact side.

It is another object of this invention to cover the non-patient contact side of this device with a water penetrable but non-hydrophilic or substantially hydrophobic material.

It is a further object of this device to reduce bulk and thickness by providing padding only on the patient contact side.

It is yet a further object of this invention to seal various layers of the device together in a manner that will allow a unitary product to be formed which may have variable outline and configuration of the device.

It is still a further object of this invention to provide a device that will allow free ingress and egress of water, into the casting layer, but which will not retain water.

These objects are meant to be illustrative and not limiting. The manner of operation, novel features and further objectives and advantages of this invention may be better understood by reference to the accompanying drawings and description.

In the exemplary embodiment, described herein, the device of this invention includes a fiber glass substrate coated or impregnated with a water hardenable synthetic prepolymer casting resin and identified herein as "casting material." A five (5) ply device is formed of the following layers listed in order from the inner patient contact layer outward to an external layer:
1. Layer 1—closed cell polyurethane foam (patient contact layer).
2. Layer 2—open cell polyurethane foam (padding layer).
3. Layer 3—non-woven polypropylene layer which may be omitted in some cases. This layer is identified herein as the inner protective layer.
4. Layer 4—casting material layer.
5. Layer 5—non-woven polypropylene layer (external protective layer).

The device so formed may be shaped, by cutting or other suitable means, into any desired outline, configuration or size. The edges of the device, after assembly, are sealed with heat and pressure. After sealing the device is placed in a waterproof container such as metallic foil, plastic, or the like to keep moisture from prematurely setting layer 4. When ready to use, the waterproof container is removed, the device is moistened and applied to the patient or workpiece, and the casting material "sets" or cures. Other casting materials, such as plaster of paris may also be used.

BRIEF DESCRIPTION OF THE DRAWINGS

FIG. 1 is a cross-sectional view of a preferred form of the device showing a five layer construction.

FIG. 2 is a perspective view of the device as applied to an arm or wrist as a splint.

FIG. 3 is a perspective view of the device in the assembly phase, showing two of the layers.

FIG. 4 is a top planar view of the device showing an illustrative form that can be assembled.

FIG. 5 is a top planar view of the device showing another illustrative form that could be assembled.

DESCRIPTION OF THE PREFERRED EMBODIMENT

FIG. 1 illustrates the preferred embodiment of my invention in cross-section. There are five (5) layers illustrated and positioned in a stack or "sandwich-like" like manner:
1. First layer formed of closed-cell polyurethane foam 20. (this is the patient contact layer).
2. Second layer formed of open-cell polyurethane foam 22 (this is the padding layer).
3. Third layer formed of non-woven polypropylene fabric 24 (this is an inner protective covering layer which may be omitted in some cases).
4. Fourth layer formed of casting material coated on or impregnated in a fiberglass substrate 26.
5. Fifth layer formed of non-woven polypropylene fabric 28 (this is the external non-patient side protective layer).

The first layer 20 is preferably a flexible material that is impervious to liquid water, but which will allow water vapor to pass through it (i.e., having a high moisture vapor transmission). This is the layer that will be in contact with the patient or workpiece. It is also preferable that this material have a smooth surface that will cause no skin irritation, and that it be formed of a material that is non-hydrophilic. Closed-cell polyurethane foam meets these criteria. Open cell polyurethane foam can also be used. Other suitable materials, such as those which function as that sold under the trademark GORE-TEX ® may be used.

The second layer 22 is preferably of a material that will not retain water (non-hydrophilic or substantially hydrophobic), but will allow water to pass through it, and which is padded so that it will conform to the patient or workpiece surface and provides comfort, resiliency and protection Open-cell polyurethane foam meets these criteria. Other suitable materials of the characteristics herein described may be used.

The third layer 24 is a flexible fabric that overlies the casting layer 26. When cured, the casting layer 26 may have irregular facets or sharp edges. Thus the fabric in this layer 24 is designed to cover these irregularities and prevent damage to the foam layer 22, or to patient surface 20. If care is taken to make a smooth cast coating material this layer 24 may be omitted. It is preferable that this layer be made of a material that will allow water to penetrate through it, so that when the unitary device is wetted, water will easily pass into the casting layer 26. It is also desirable that this layer 24 not retain any water itself (i.e., non-hydrophilic or substantially hydrophobic), so that the device will not become water logged and require "wringing" or prolonged drying times. Non-woven polypropylene fabric meets these criteria. Other suitable materials may be used, and as noted above, this layer 24 may be omitted.

The fourth layer 26 is the casting material layer. It is this layer that, when wetted, will cause the resin to cure and form the rigid portion of the cast or splint when the resin dries or cures. Polymer materials such as disclosed in U.S. Pat. Nos. 4,411,262 and 4,502,479 are exemplary of reactive hardenable resins disclosed for use in orthopedic bandages or casting tapes cured with water. See also the teachings of U.S. Pat. No. 4,442,833 all of above patents being incorporated herein by reference. Other casting compounds such as plaster of paris may also be used in this device. Preferably, this fourth layer 26 is formed of a support substrate, such as a woven or knitted fiberglass fabric, or other suitable substrate, and is coated or impregnated with the casting compound (resin, plaster, etc.), that can be activated by the addition of water. Thus, it is important that the surrounding layers allow water to pass freely into this layer 26 when the device is wetted so that activation can occur. It is also important (as noted above) that the surrounding layers not retain excessive water themselves, to prevent the device from becoming "waterlogged." This layer 26 is formed so as to be slightly smaller than the other layers in outline to facilitate peripheral sealing, as will be noted below. The casting material must be kept dry until ready to use; this is accomplished by sealing the device in a waterproof package after assembly—not shown.

The fifth layer 28 is the outer layer of the device, and preferably is formed of the same material as the third layer 24 (non-woven polypropylene fabric). This layer 28 functions to cover the casting layer 26, protects and, when the device is sealed, keeps the casting layer in place. It is desirable that this layer allow water to pass freely into the casting layer 26 when the device is wetted, yet not retain significant water itself (non-hydrophilic). It is also a function of this layer 28 to be of sufficient strength to contain any sharp edges or facets formed by the casting layer 26 when cured.

Once the above layers 20, 22, 24, 26, and 28 are assembled, the edges of layers 20, 22, 24, and 28 are sealed such as by means such as heat and pressure as shown at number 30, thereby enclosing the casting layer 26 and forming a unitary product or device. It is another feature of the preferably selected materials for layers 20, 22, 24, and 28 that they be easily heat and pressure sealed; thus, these layers are also slightly larger in outline than the casting layer 26 so that the sealed edges and ends will be peripheral to the edges of the casting layer 26. Other means of sealing such as adhesives, sewing, and the like may be used. Since this product does not use a sheath or other form constricting or confining means, the outline and configuration of the device may be any shape, as illustrated in FIGS. 4 and 5. The completed device is then sealed in a waterproof container, such as metallic foil, plastic or the like (not shown) until ready to use.

To assemble the device, fiberglass mesh substrate is impregnated or coated with dry prepolymer casting resin (or other casting material) and cut or otherwise shaped into the desired outline, which forms the casting layer 26. All of the remaining layers are then cut or fashioned to be slightly larger than the casting layer 26 so that their edges extend beyond the edges of the casting layer. I have found that approximately a one (1) centimeter overlay is usually sufficient, but this can vary depending on the size of the unitary device and the width of the seal desired. The layers are then assembled in the order described above. The overlapping edges are then sealed or fused together with heat and pressure. The device is then sealed in a waterproof container until ready for use. Thus, the device may be of irregular outline in a single use package, or it may be an elongate roll from which suitable portions are cut as needed and the package then resealed.

To use this device, the waterproof container is opened, the device is removed and wetted (by immersion, spraying, or the like), applied and molded to the patient or workpiece contours, and allowed to dry or cure.

FIG. 2 illustrates this device, generally indicated by 40, applied to an arm 42. In this application the device 40 has been used to form a splint, conforming to the lower portion of the arm 42 and bending upward into the palm of the hand at 44 to form a piece for gripping by the fingers 46. Bandage material (not shown) may be wrapped around the arm and splint to hold same in place.

FIG. 3 illustrates the device 40 in the construction phase, where the fifth layer 28 has been placed over the casting layer 26. It is noted that the outer layer 28 is larger and overlaps the casting layer 26, so that the edges of layer 28 and the other layers 20, 22, and 24 (not shown in this figure), may be sealed around the casting layer 26 retaining it in the center of the device.

FIGS. 4 and 5 illustrate some representative shapes that may be formed using the teachings herein. FIG. 4, for example, could be used in the arm application shown in FIG. 2. FIG. 5 could be used as a splint with the arms of the "T" securing the splint to the hand or wrist.

This product or device may be made and packaged as individual units, or it may be formed into multiuse units. As a single use unit, the product would be shaped in a selected configuration and wrapped in its waterproof package which would be a single one-use device. In the multiuse application, the device can be formed into a long roll, and the amount needed cut off, and the package resealed. Alternatively, a plurality of sealed single use units can be connected together in a strip or roll, with a tearable or perforated connection between each for easy separation (not illustrated).

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

What is claimed is:

1. A unitary casting device, for making casts and splints, comprising:
   a patient contact layer formed of material that is impervious to liquid water but is penetrable by water vapor;
   a padding layer, juxtaposed against said patient contact layer, and formed of padded material;
   a casting layer, placed along said padding layer, and formed of a water activated casting material;
   an outer protective layer, juxtaposed against said casting layer, and formed of a non-hydrophilic but water penetrable material; and
   means for holding said layers together to form said unitary device.

2. The unitary casting device, as described in claim 1, wherein said patient contact layer is formed of closed cell polyurethane foam.

3. The unitary casting device, as described in claim 1, wherein said patient contact layer is formed of open cell polyurethane foam.

4. The unitary casting device, as described in claim 1, wherein said padding layer is formed of open cell polyurethane foam.

5. The unitary casting device, as described in claim 1, wherein said casting layer is formed of fiberglass substrate impregnated and coated with synthetic casting resin.

6. The unitary casting device, as described in claim 5, wherein said synthetic casting resin is a water curable polyurethane prepolymer resin.

7. The unitary casting device, as described in claim 1, wherein said casting layer is formed of a substrate coated with plaster of paris.

8. The unitary casting device, as described in claim 1, wherein said outer protective layer is formed of nonwoven polypropylene.

9. The unitary casting device, as described in claim 1, wherein said means for holding is sealing caused by a combination of heat and pressure.

10. The unitary casting device, as described in claim 1, wherein an inner protective layer is placed between said padding layer and said casting layer.

11. A unitary casting device, for making casts and splints, comprising:
    a patient contact layer formed of material that is impervious to liquid water but is penetrable by water vapor;
    a padding layer, juxtaposed against said patient contact layer, and formed of padded material;
    a casting layer, placed along said padding layer, and formed of a water activated casting material;

an inner protective layer, placed between said padding layer and said casting layer, said inner protective layer is formed of non-woven polypropylene;

an outer protective layer, juxtaposed against said casting layer, and formed of a non-hydrophilic but water penetrable material; and means for holding said layers together to form said unitary device.

12. The unitary casting device, as described in claim 1, further including a waterproof package suitable for containing said device and keeping it moisture free until such time as it is to be used.

13. The device, as described in claim 12, in which said waterproof package is formed of metallic foil.

14. A unitary casting device, comprising:

a flat planar longitudinal section of substrate, said substrate defining a first side and a second side joined by edges;

a reactive material impregnated into or coated onto said substrate which when exposed to sufficient liquid moisture will form a rigid self supporting structure;

a longitudinal enclosure overlying said edges of said impregnated substrate comprised of:

along said first side a first covering of a thin layer of a polyurethane foam, it's outer side being covered with a material that is impermeable to liquid moisture, but permeable to moisture vapor;

along said second side a second covering of non-woven liquid and vapor moisture permeable material; and means to join said first and second coverings along and outside of said edges.

15. The device of claim 14 including a protective and sealed moisture-impervious outer package for said device.

16. The device of claim 14 wherein said means for joining said first and second convergings is by a heat seal.

17. The device of claim 14 wherein said first covering on said first side of the polyurethane foam layer, is a layer of closed cell polyurethane foam.

18. The device of claim 14 wherein said reactive material is a water activated prepolymer resin.

19. The device of claim 14 wherein said second covering along said second side is a non-woven polypropylene material.

20. The method of making a unitary casting device, suitable for use in making casts and splints, comprising the steps of:

impregnating a sheet of substrate having a first side and a second side with dry casting material forming a casting layer;

covering said impregnated sheet with a sheet of non-padded water permeable non-hydrophilic material on said first side;

placing a sheet of padded water permeable non-hydrophilic material having a first side and a second side in juxtaposition so that said first side of said padded material is against said second side of said impregnated sheet of casting material;

overlaying said second side of said sheet of padded material with a sheet of non-hydrophilic material that is impervious to liquid water, but permeable to water vapor;

trimming said sheets into the desired shape and configuration;

sealing the edges of said sheets together by means of heat and pressure thus forming a unitary device; and placing said unitary device in a waterproof package that can be sealed until usage of the device.

21. The method of claim 20, wherein said sheet of substrate is formed of fiberglass mesh impregnated or coated with a dry water actuated synthetic prepolymer resin.

22. The method of claim 20, wherein said dry casting material is plaster of paris.

23. The method of claim 20, wherein said sheet of non-padded water permeable material is formed of non-woven polypropylene.

24. The method of claim 20, wherein said sheet of padded material is formed of open cell polyurethane foam.

25. The method of claim 20, wherein said sheet of material that is impervious to liquid water, but permeable to water vapor is formed of closed cell polyurethane foam.

26. The method of claim 20, wherein said waterproof package is formed of metallic foil.

27. A unitary casting device, suitable for making casts and splints, comprising:

a first layer formed of closed cell polyurethane foam;

a second layer formed of open cell polyurethane foam, juxtaposed against said first layer;

a third layer formed of non-woven polypropylene fabric, juxtaposed against said second layer;

a fourth layer formed of fiberglass mesh coated with dry water actuated prepolymer synthetic casting resin, juxtaposed against said third layer;

a fifth layer formed of non-woven polypropylene fabric, juxtaposed against said fourth layer;

a peripheral seal, formed by heat and pressure, joining said first, second, third and fifth layers together so as to enclose said forth layer therein forming said unitary device; and means for packaging said unitary device so as to exclude water therefrom until ready for use.

28. The device, as described in claim 27, further including a means for shaping said device into any desired configuration.

29. The device, as described in claim 27, wherein said packaging means is metallic foil.

* * * * *